US00PP27831P3

(12) United States Plant Patent
Pineau

(10) Patent No.: US PP27,831 P3
(45) Date of Patent: Apr. 4, 2017

(54) ***BERBERIS* PLANT NAMED 'ORANGE TORCH'**

(50) Latin Name: *Berberis thunbergii*
Varietal Denomination: Orange Torch

(71) Applicant: Pépinières Minier S.A., Beaufort-en-Vallée (FR)

(72) Inventor: Patrick Pineau, Saint-Mathurin-sur-Loire (FR)

(73) Assignee: Pépinières Minier S.A., Beaufort-en-Vallée (FR)

( * ) Notice: Subject to any disclaimer, the term of this patent is extended or adjusted under 35 U.S.C. 154(b) by 0 days.

(21) Appl. No.: 14/756,841

(22) Filed: Oct. 21, 2015

(65) Prior Publication Data

US 2016/0374242 P1 Dec. 22, 2016

Related U.S. Application Data

(60) Provisional application No. 62/230,909, filed on Jun. 18, 2015.

(51) Int. Cl.
*A01H 5/02* (2006.01)

(52) U.S. Cl.
USPC ..... Plt./241

(58) Field of Classification Search
USPC ..... Plt./241
See application file for complete search history.

*Primary Examiner* — Annette Para
(74) *Attorney, Agent, or Firm* — Audrey Charles

(57) ABSTRACT

A new and distinct cultivar of *Berberis* plant named 'Orange Torch', characterized by spring foliage color of medium yellow and yellow-green tinted with red-orange, bright red young stem color; and moderately vigorous, compact, narrowly-upright growth habit, is disclosed.

1 Drawing Sheet

Latin name of genus and species of plant claimed: *Berberis thunbergii.*

Variety denomination: 'Orange Torch'.

BACKGROUND OF THE INVENTION

The present invention relates to a new and distinct cultivar of *Berberis* plant botanically known as *Berberis thunbergii* and hereinafter referred to by the cultivar name 'Orange Torch'.

The new *Berberis* cultivar is a naturally-occurring sport of GOLDEN TORCH 'Torchd'or', not patented, characterized by its yellow and yellow-green colored foliage typically having pink-red tips in autumn, and moderately vigorous, compact, narrowly-upright growth habit. The new cultivar was discovered as a side shoot and selected during July 2007 in a controlled environment in La Menitre, Maine et Loire, France.

Asexual reproduction of the new cultivar by terminal stem cuttings since July 2007 in La Menitre, Maine et Loire, France and Mount Angel, Oreg. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Orange Torch' as a new and distinct cultivar of *Berberis* plant:

1. Spring foliage color of medium yellow and yellow-green tinted with red-orange;
2. Bright red young stem color; and 3. Moderately vigorous, compact, narrowly-upright growth habit.

Plants of the new cultivar differ from plants of the parent primarily in foliage color.

Of the many commercially available *Berberis* cultivars, the most similar in comparison to the new cultivar is 'Orange Rocket', U.S. Plant Pat. No. 18,411. However, in side by side comparisons, plants of the new cultivar differ from plants of 'Orange Rocket' in at least the following characteristics:

1. Plants of the new cultivar have spring and summer foliage colors different from plants of 'Orange Rocket', and
2. Plants of the new cultivar are more vigorous than plants of 'Orange Rocket'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs may differ slightly from the color values cited in the detailed description, which accurately describes the colors of 'Orange Torch'. The plants are approximately one-year old and were grown for three months in a greenhouse in West Chicago, Ill. The flower photograph was taken in May 2016 from two-year old plants grown outdoors in West Chicago, Ill.

DETAILED BOTANICAL DESCRIPTION

Figure 1:
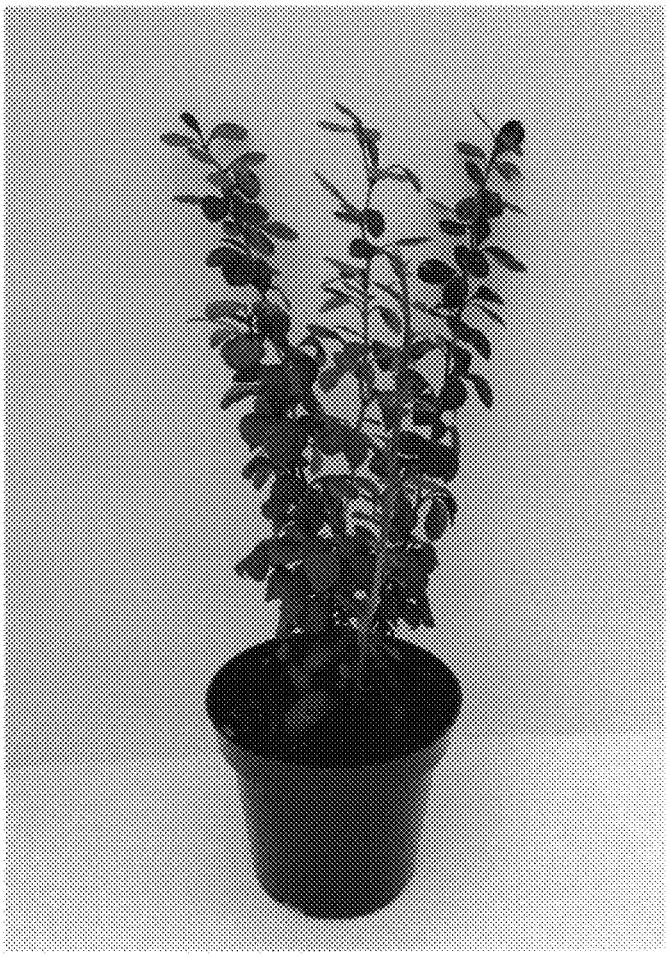
FIG. 1 illustrates a side view of the overall growth and habit of 'Orange Torch'.
Figure 2:
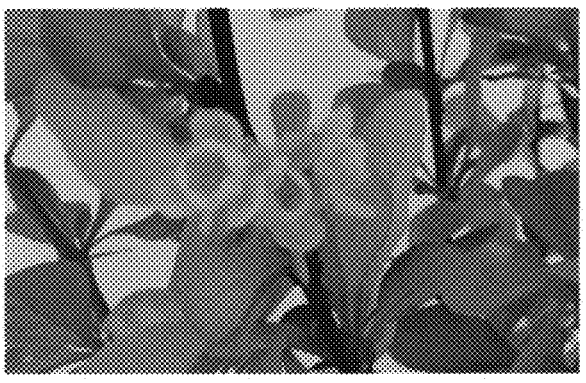
FIG. 2 illustrates a close-up view of the inflorescences of 'Orange Torch'.

The new cultivar has not been observed under all possible environmental conditions to date. Accordingly, it is possible that the phenotype may vary somewhat with variations in the environment, such as temperature, light intensity, and day length, without, however, any variance in genotype.

The Chart used in the identification of colors described herein is The R.H.S. Colour Chart of The Royal Horticultural Society, London, England, 2007 edition, except where general color terms of ordinary significance are used. The color values were determined in September 2015 under natural light conditions in West Chicago, Ill.

The following descriptions and measurements describe approximately one-year old plants produced from cuttings from stock plants and grown under conditions comparable to those used in commercial practice. Plants were pinched when transplanted into a soilless growth medium in 4.5 inch containers in a West Chicago, Ill. glass-covered greenhouse. Greenhouse temperatures were maintained at approximately 70° F. to 75° F. (21° C. to 24° C.) during the day and approximately 58° F. to 62° F. (14° C. to 17° C.) during the night. No supplemental lighting was provided. Flower data was taken in May 2016 from two-year old plants grown outdoors in West Chicago, Ill. Measurements and numerical values represent averages of typical plants.

Botanical classification: *Berberis thunbergii* cultivar Orange Torch.

Parentage:

*Parent*.—GOLDEN TORCH 'Torchd'or', not patented.

Propagation:

*Type*.—Softwood stem cuttings.

*Time to initiate roots*.—Approximately 70 days.

*Time to produce a rooted cutting*.—Approximately one year.

*Root description*.—Fine to medium; somewhat fleshy and fibrous; yellow to light brown in color.

*Rooting habit*.—Freely branching; moderate density.

Plant description:

*Commercial crop time*.—Approximately 24 months from a rooted cutting to finish in a 15 cm pot.

*Plant type*.—Deciduous shrub.

*Growth habit and general appearance*.—Moderately vigorous, compact, narrowly-upright growth habit.

*Cold hardiness*.—At least in U.S.D.A. Zone 4.

*Size*.—Height: Approximately 26.0 cm. Width: Approximately 21.0 cm.

*Branching habit*.—Freely branching, pinching enhances basal branching. Quantity of main lateral branches per plant: Approximately 5.

*Branch*.—Strength: Strong. Length: Approximately 23.0 cm. Diameter: Approximately 2.0 mm. Length of central internode: Approximately 1.3 cm. Texture: Deeply grooved. Color of young stems: 144B with and overlay of 185A. Color of mature stems: 144A with an overlay of 187A, becoming N199D with age.

Foliage description:

*General description*.—Quantity of leaves per main branch: Approximately 56 in 14 clusters. Fragrance: None detected. Form: Simple. Arrangement: Alternate, clustered in whorls of four.

*Leaves*.—Shape: Obovate to spatulate. Margin: Entire. Apex: Rounded to broadly acute. Base: Attenuate, sessile. Venation pattern: Pinnate. Length of mature leaf: Approximately 3.5 cm. Width of mature leaf: Approximately 1.8 cm. Texture of upper and lower surfaces: Glabrous. Color of upper surface of developing leaves: 144B with an overlay of 185A; in spring 1C with an overlay of 34A to 34D. Color of lower surface of developing leaves: Closest to 191B; in spring 1C with an overlay of 34A to 34D. Color of upper surface of fully-expanded leaves: 137B with an overlay of 187A, venation 137B and 187A; in spring 1C and 145A with an overlay of 34A to 34D; in fall most leaves transition to 34A to 34C. Color of lower surface of fully expanded leaves: Closest to 191B with midvein of 147D; in spring 1C and 145A with an overlay of 34A to 34D; in fall most leaves transition to 34A to 34C.

*Spine*.—Length: Approximately 7.0 mm. Diameter: Less than 1.0 mm. Texture: Glabrous. Color: Close to 164A with tips of 203A.

Flowering description:

*Flowering habit*.—Flowers are observed in the spring on second-year growth and are ornamentally insignificant, self-cleaning.

*Lastingness of inflorescence on the plant*.—Approximately 2 weeks.

*Lastingness of individual flower on the plant*.—Approximately 4 to 5 days.

Inflorescence description:

*General description*.—Type: Drooping umbrella-shaped clusters located in leaf axils. Quantity per plant: Approximately 10. Quantity flowers per cluster: Approximately 2 to 3. Diameter: Approximately 1.8 cm. Depth: 1.1 cm. Fragrance: None detected.

*Peduncle*.—Strength: Strong. Length: Approximately 1.0 cm. Diameter: Approximately 1.0 mm Texture: Glabrous. Color: 144B tinted with 187B.

Flower description:

*Type*.—Single, cup-shaped.

*Bud*.—Rate of opening: Generally takes 2 to 3 days for bud to progress from first color to fully open flower. Quantity per plant: Approximately 10.

*Bud just before opening*.—Shape: Globular. Length: Approximately 3.0 mm. Width: Approximately 4.0 mm. Texture: Glabrous. Color of petals: 4D. Color of sepals: 144A with 151A.

*Corolla*.—Diameter: Approximately 9.0 mm. Depth: Approximately 5.0 mm.

*Petals*.—Quantity: 6 in a single whorl. Shape: Orbicular, cupped. Appearance: Dull. Margin: Entire. Apex: Rounded to erose. Length: Approximately 4.0 mm. Width: Approximately 3.0 cm. Texture of upper and lower surfaces: Glabrous. Color of upper surface when first and fully open: 2D with center region of 1C to 1D. Color of lower surface when first and fully open: 2D with center region of 1C to 1D.

*Calyx*.—Shape: cup-shaped, opening with age. Diameter: Approximately 9.0 mm. Depth: Approximately 4.0 mm.

*Sepals*.—Quantity per flower: 6, in 2 whorls of 3. Shape: Roughly orbicular, innermost petal-like. Apex of outermost: Broadly acute to rounded. Apex of innermost: Rounded to erose. Base of all: Rounded. Length of outermost: Approximately 4.0 mm. Width of outermost: Approximately 3.0 mm. Length of innermost: Approximately 5.0 mm. Width of innermost: Approximately 4.0 mm. Texture of upper and lower surfaces of all: Glabrous. Color of upper and lower surfaces of outermost: Margins of NN155A, centers of 144A with 151A, upper surface tinted with 187C. Color of upper and lower surfaces of innermost: Margins of NN155A, centers of 1C, apex of upper surface occasionally lightly tinted with 187C, venation of 151A.

*Bracts*.—Quantity per flower: 2, at base of each flower. Shape: Ovate, positioned horizontally. Apex: Acute. Base: Truncate. Length: Approximately 4.0 mm. Width: Approximately 1.5 mm. Texture of upper and lower surfaces: Glabrous. Color of upper and lower surfaces: 144A with 151A, tinted at apex with 187C.

*Pedicels*.—Strength: Strong, flexible. Length: Approximately 3.0 to 4.0 mm. Diameter: Approximately 1.0 mm. Texture: Glabrous. Color: 144B heavily tinted with 187B.

*Reproductive organs*.—Androecium: Stamen quantity: 6. Stamen length: Approximately 3.0 mm. Filament color: 4C. Anther shape: Two-valved. Anther length: Approximately 1.0 mm. Anther color: 4B. Pollen amount: Abundant. Pollen color: 4C. Gynoecium: Pistil quantity: 1 per flower. Pistil length: Approximately 3.0 mm. Stigma shape: Flattened globose with a central depression. Stigma length: Less than 1.0 mm. Stigma diameter: 1.5 mm. Stigma color: N144A. Style length: Less than 1.0 mm. Style color: 144B. Ovary length: Approximately 2.5 mm. Ovary color: N144A.

Seed and fruit production: Neither seed nor fruit production has been observed.

Disease and pest resistance: Resistance to pathogens and pests common to *Berberis* has not been observed.

What is claimed is:

1. A new and distinct cultivar of *Berberis* plant named 'Orange Torch', substantially as herein illustrated and described.

* * * * *